US00PP20607P2

(12) United States Plant Patent
Hofmann

(10) Patent No.: US PP20,607 P2
(45) Date of Patent: Dec. 22, 2009

(54) ***BEGONIA* PLANT NAMED 'INNBOLPINK'**

(50) Latin Name: *Begonia×tuberhybrida*
Varietal Denomination: Innbolpink

(75) Inventor: Silvia Hofmann, Mainz (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 12/286,070

(22) Filed: Sep. 26, 2008

(51) Int. Cl.
*A01H 5/00* (2006.01)

(52) U.S. Cl. ..... Plt./348

(58) Field of Classification Search ..... Plt./348

See application file for complete search history.

*Primary Examiner*—Kent L Bell
(74) *Attorney, Agent, or Firm*—C. A. Whealy

(57) ABSTRACT

A new and distinct cultivar of *Begonia* plant named 'Innbolpink', characterized by its compact and mounded to trailing plant habit; freely branching habit; dense and bushy growth habit; medium green-colored leaves; and numerous single flowers that are bright pink in color.

1 Drawing Sheet

Botanical designation: *Begonia×tuberhybrida.*
Cultivar denomination: 'Innbolpink'.

BACKGROUND OF THE INVENTION

The present invention relates to a new and distinct cultivar of *Begonia* plant, botanically known as *Begonia×tuberhybrida* and hereinafter referred to by the name 'Innbolpink'.

The new *Begonia* plant is a product of a planned breeding program conducted by the Inventor in Gensingen, Germany. The objective of the breeding program was to develop new compact *Begonia* cultivars with attractive single flowers.

The new *Begonia* plant originated from a cross-pollination made by the Inventor in January, 2005 of a proprietary selection of *Begonia×tuberhybrida* identified as code number B 04 19-1, not patented, as the female, or seed, parent with *Begonia×tuberhybrida* 'Weiβ 1', not patented, as the male, or pollen, parent. The new *Begonia* was discovered and selected by the Inventor as a single plant from within the progeny of the stated cross-pollination in a controlled greenhouse environment in Gensingen, Germany in September, 2005.

Asexual reproduction of the new *Begonia* plant by vegetative cuttings in a controlled greenhouse environment in Gensingen, Germany since October, 2005, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Innbolpink'. These characteristics in combination distinguish 'Innbolpink' as a new and distinct cultivar of *Begonia:*

1. Compact and mounded to trailing plant habit.
2. Freely branching habit; dense and bushy growth habit.

3. Medium green-colored leaves.
4. Numerous single flowers that are bright pink in color.

Plants of the new *Begonia* differ from plants of the female parent selection in the following characteristics:

1. Plants of the new *Begonia* are more compact than and not as vigorous as plants of the female parent selection.
2. Plants of the new *Begonia* are more freely branching than plants of the female parent selection.

Plants of the new *Begonia* differ from plants of the male parent, 'Weiβ 1' in the following characteristics:

1. Plants of the new *Begonia* are more freely branching than plants of 'Weiβ 1'.
2. Plants of the new *Begonia* have single flowers whereas plants of 'Weiβ 1' have double flowers.
3. Plants of the new *Begonia* and 'Weiβ 1' differ in flower color as plants of 'Weiβ 1' have white-colored flowers.

Plants of the new *Begonia* can also be compared to plants of the *Begonia×tuberhybrida* 'Bonfire', disclosed in U.S. Plant Pat. No. 15,108. In side-by-side comparisons conducted in Gensingen, Germany, plants of the new *Begonia* differed from plants of 'Bonfire' in the following characteristics:

1. Plants of the new *Begonia* were more compact and mounded than plants of 'Bonfire'.
2. Plants of the new *Begonia* were more freely branching and denser than plants of 'Bonfire'.
3. Plants of the new *Begonia* and 'Bonfire' differed in flower color as plants of 'Bonfire' had orange-colored flowers.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the color values cited in the detailed botanical description which accurately describe the colors of the new *Begonia* plant.

The photograph at the bottom of the sheet comprises a side perspective view of a typical flowering plant of 'Innbolpink' grown in a container.

The photograph at the top of the sheet is a close-up view of typical flowers and leaves of 'Innbolpink'.

DETAILED BOTANICAL DESCRIPTIONS

Plants used for the aforementioned photographs and following observations and measurements were grown in Bonsall, Calif. in one-gallon containers and under commercial practice in a shaded polyethylene-covered greenhouse during the late summer. During the production of the plants, day temperatures ranged from 18° C. to 35° C., night temperatures ranged from 10° C. to 24° C. Plants used for the photographs and the description were pinched one time and were twelve weeks from planting. In the following description, color references are made to The Royal Horticultural Society Colour Chart, 2001 Edition, except where general terms of ordinary dictionary significance are used.

Botanical classification: *Begonia×tuberhybrida* 'Innbolpink'.

Parentage:

*Female, or seed, parent.*—Proprietary selection of *Begonia×tuberhybrida* identified as code number B 04 19-1, not patented.

*Male, or pollen, parent.*—*Begonia×tuberhybrida* 'Weiβ 1', not patented.

Propagation:

*Type.*—By vegetative cuttings.

*Time to initiate roots, summer.*—About 7 to 10 days at temperatures of about 18° C. to 24° C.

*Time to initiate roots, winter.*—About 9 to 14 days at temperatures of about 18° C. to 24° C.

*Time to produce a rooted young plant, summer.*—About four weeks at temperatures of about 18° C. to 24° C.

*Time to produce a rooted young plant, winter.*—About five weeks at temperatures of about 18° C. to 24° C.

*Root description.*—Fine, fibrous; white in color. Plants of the new *Begonia* have not been observed to form tubers.

*Rooting habit.*—Moderate branching; moderately dense.

Plant description:

*Plant and growth habit.*—Compact and mounded to trailing plant habit; freely branching with about seven to eight branches per plant; dense and bushy growth habit; vigorous growth habit.

*Plant height.*—About 22 cm.

*Plant width.*—About 25 cm by 28 cm.

*Branch description.*—Length: About 21 cm. Diameter: About 7 mm. Internode length: About 3 cm. Texture: Smooth, glabrous. Color: Close to 199A tinted with close to 182B.

*Leaf description.*—Arrangement: Alternate; simple. Length: About 10.2 cm. Width: About 3.9 cm. Shape: Lanceolate; asymmetrical. Apex: Acute. Base: Oblique. Margin: Bi-serrate. Texture, upper and lower surfaces: Smooth, glabrous. Venation pattern: Palmate; reticulate. Color: Developing leaves, upper surface: Close to 146A. Developing leaves, lower surface: Close to 183D. Fully expanded leaves, upper surface: Close to 137A; at the margins, close to 183B; venation, close to 137A. Fully expanded leaves, lower surface: Close to 148A; venation, close to 148B. Petiole length: About 2 cm. Petiole diameter: About 2.5 mm. Petiole texture, upper and lower surfaces: Smooth, glabrous. Petiole color, upper surface: Close to 177B. Petiole color, lower surface: Close to 199B.

Flower description:

*Flowering habit.*—Actinomorphic single flowers; flowers axillary in clusters of typically three; staminate and pistillate flowers observed. Freely flowering habit with about seven to nine flowers and flower buds per lateral branch. Flowers drooping.

*Fragrance.*—None detected.

*Natural flowering season.*—Plants flower continuously from April to October in Germany. Flowers last about two to three days on the plant; flowers not persistent.

*Flower buds.*—Shape: Elliptic. Length: About 2.4 cm. Diameter: About 1.1 cm. Color: Close to 54C.

*Flowers, staminate flowers.*—Diameter: About 3.4 cm. Depth (height): About 2.8 cm.

*Flowers, pistillate flowers.*—Diameter: About 4 cm. Depth (height): About 3.5 cm.

*Tepals, staminate flowers.*—Quantity/arrangement: Four in a single whorl. Length: About 2.4 cm to 2.5 cm. Width: About 7 mm to 9 mm. Shape: Elliptic to narrowly elliptic. Apex: Acute. Base: Truncate. Margin: Entire. Texture, upper and lower surfaces: Smooth, glabrous; velvety. Color: When opening, upper surface: Close to 55B. When opening, lower surface: Close to 55C. Fully opened, upper surface: Close to 54A; color does not fade with development. Fully opened, lower surface: Close to 54B.

*Tepals, pistillate flowers.*—Quantity/arrangement: Five in a single whorl. Length: About 3.4 cm. Width: About 1.1 cm. Shape: Elliptic to narrowly elliptic. Apex: Acute. Base: Truncate. Margin: Entire. Texture, upper and lower surfaces: Smooth, glabrous; velvety. Color: When opening, upper surface: Close to 55B. When opening, lower surface: Close to 55C. Fully opened, upper surface: Close to 54A; color does not fade with development. Fully opened, lower surface: Close to 54B.

*Flower bracts.*—None observed.

*Peduncles.*—Angle: About 30° to 45° from the stem axis. Length: About 1.7 cm to 2.6 cm. Diameter: About 1.5 mm. Texture: Smooth, glabrous. Color: Close to 64D.

*Reproductive organs.*—Stamens (present on staminate flowers only): Quantity per flower: About 75. Filament length: About 1 mm. Filament color: Close to NN155D. Anther shape: Oval. Anther length: About 1.5 mm. Anther color: Close to 2C. Pollen amount: Sparse. Pollen color: Close to 2C. Pistils (present on pistillate flowers only): Pistil length: About 1.8 cm. Stigmas per flower: Six. Stigma color: Close to 16A. Style length: About 2 mm. Style color: Close to 24C. Ovary color: Close to 145C.

*Seed/fruit.*—Seed and fruit production have not been observed.

Disease/pest resistance: Plants of the new *Begonia* not been observed to be resistant to pathogens and pests common to *Begonia*.

Temperature tolerance: Plants of the new *Begonia* have been observed to tolerate temperatures from about 5° C. to about 35° C.

It is claimed:

1. A new and distinct *Begonia* plant named 'Innbolpink' as illustrated and described.

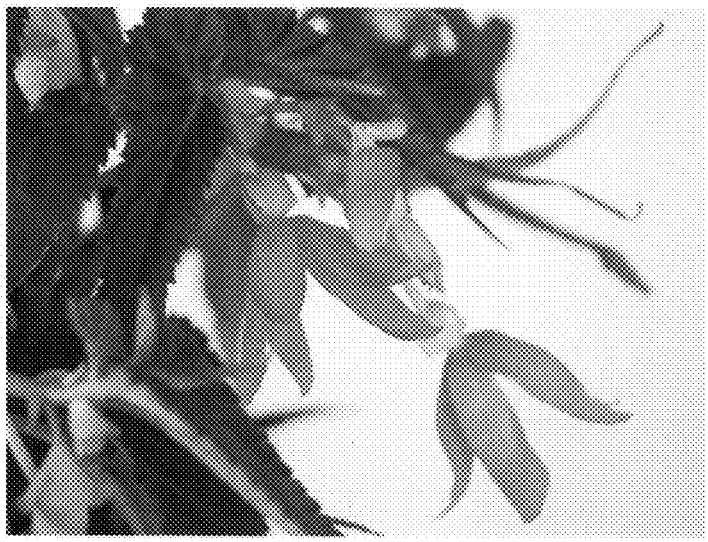
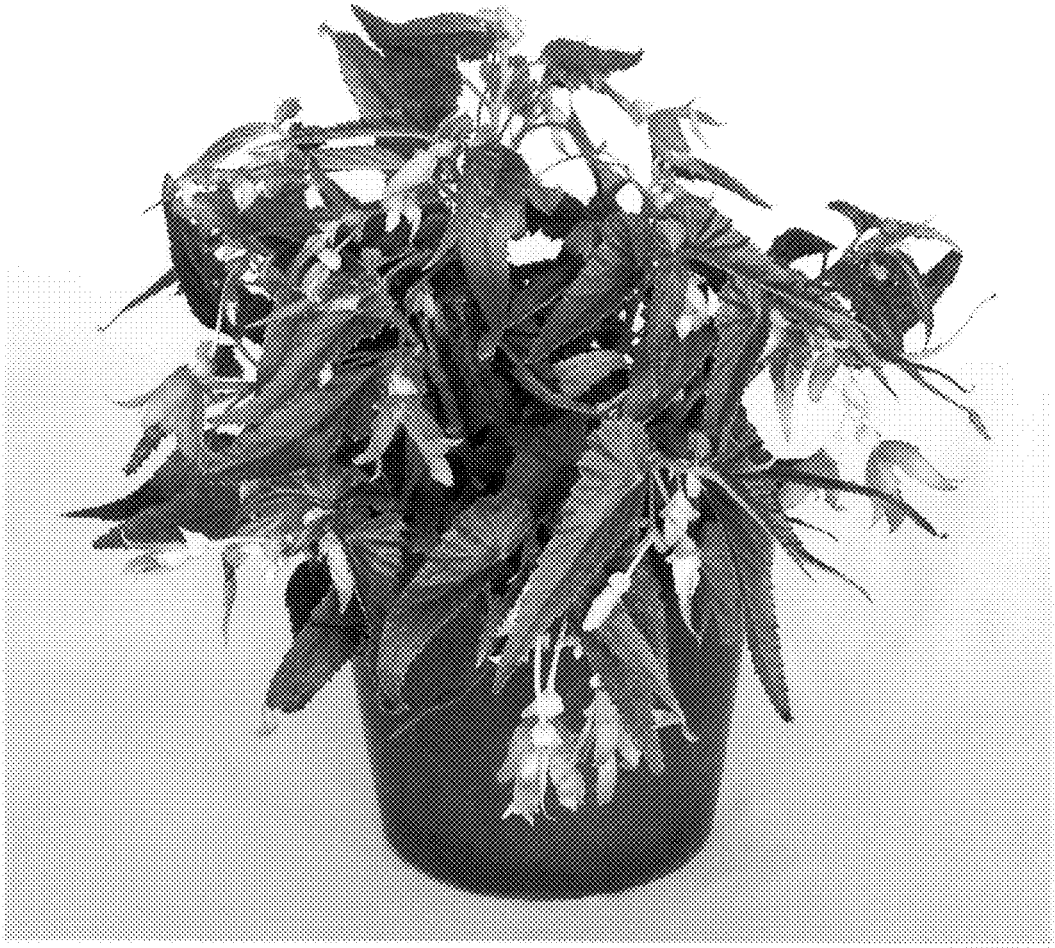

* * * * *